US006746873B1

(12) United States Patent
Buchanan et al.

(10) Patent No.: US 6,746,873 B1

(45) Date of Patent: Jun. 8, 2004

(54) VIBRATORY SYSTEM FOR A SORTING FLOW CYTOMETER

(75) Inventors: Kristopher S. Buchanan, Fort Collins, CO (US); Lisa Herickhoff, Fort Collins, CO (US); George Seidel, LaPorte, CO (US); George C. Malachowski, Fort Collins, CO (US); Matthias J. G. Ottenberg, Fort Collins, CO (US); Douglas H. Ferguson, Eden Valley, MN (US)

(73) Assignees: XY, Inc., Fort Collins, CO (US); DakoCytomation Colorado, Inc., Fort Collins, CO (US); Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 09/622,621

(22) PCT Filed: Feb. 19, 1999

(86) PCT No.: PCT/US99/03638

§ 371 (c)(1),
(2), (4) Date: Sep. 18, 2000

(87) PCT Pub. No.: WO99/42810

PCT Pub. Date: Aug. 26, 1999

Related U.S. Application Data

(60) Provisional application No. 60/075,612, filed on Feb. 20, 1998.

(51) Int. Cl.$^{7}$ ................................................ G01N 33/48

(52) U.S. Cl. ....................... 436/63; 422/82.01; 209/3.1; 209/3.2; 209/4; 209/571; 209/127.4

(58) Field of Search ................ 436/63, 164; 422/82.01, 422/82.05; 356/72, 73; 250/461.2; 209/3.1, 3.2, 4, 571, 576–579, 127.4

(56) References Cited

U.S. PATENT DOCUMENTS

| | | | | | |
|---|---|---|---|---|---|
| 4,487,320 | A | * | 12/1984 | Auer | 209/3.1 |
| 4,673,288 | A | | 6/1987 | Thomas et al. | 356/72 |
| 4,790,653 | A | | 12/1988 | North, Jr. | 356/73 |
| 4,981,580 | A | * | 1/1991 | Auer | 209/3.1 |
| 5,602,039 | A | | 2/1997 | Van den Engh | 436/164 |
| 5,641,457 | A | | 6/1997 | Vardanega et al. | 422/82.01 |
| 5,643,796 | A | | 7/1997 | Van den Engh et al. | 436/50 |

FOREIGN PATENT DOCUMENTS

| | | | |
|---|---|---|---|
| EP | 461618 | * | 12/1991 |
| WO | 96/12171 | * | 4/1996 |

* cited by examiner

*Primary Examiner*—Maureen M. Wallenhorst
(74) *Attorney, Agent, or Firm*—Santangelo Law Offices, P.C

(57) ABSTRACT

A flow cytometry system is disclosed for oscillating the exterior of a flow cytometer nozzle. Oscillating the exterior of a flow cytometer nozzle at selected oscillations or a sweeping range of oscillations disintegrates particles and gas entrapped within the flow cytometer nozzle. Adherents absorbed to the exterior of the flow cytometer nozzle may also be removed. An energy source (1) serves to generate a selected oscillation or range of oscillations. The energy source (1) is connected to a flexible transfer element (2) which conducts the electrical signals to an oscillation system (3). The oscillation system (3) turns the electrical energy from the energy source (1) into mechanical oscillations and is connected to a portable device (4) which disintegrates particles, dislocates gas within the flow cytometer nozzle and cleans the exterior of the flow cytometer aperture.

104 Claims, 8 Drawing Sheets

VIBRATORY SYSTEM FOR A SORTING FLOW CYTOMETER

This application is the National Stage of International Application No. PCT/US99/03638, filed Feb. 19, 1999 which claims benefit of U.S. Provisional application No. 60/075,612, filed Feb. 20, 1998, each hereby incorporated by reference.

I. TECHNICAL FIELD

This invention relates to a flow cytometry system and methods of operating both analytical and drop flow cytometers including apparatus and methods of unclogging or dislodging of media or gas from the inside of devices which may become clogged, Specifically, the invention focuses upon a device which may be used to unclog nozzles, dislocate gas, or clean exterior surfaces of flow cytometers used in the cytometry industry, which are subject to clogging, entrapping gas, or collecting adherents to exterior surfaces.

II. BACKGROUND

The desire to unclog, dislocate entrapped gas, and clean nozzles or a nozzle body has been known in some industries for many years. This desire has been quite acute for quite some time in the cytometry field. Cytometers are sometimes used to separate or sort particles from one another based upon the differences detected by shining a high intensity light upon each particle then discerning differences between the amount of light reflected from each particle. These particles may be quite variable based upon the application of the user. They may be biological cells of plant or animal matter or particles of other materials. All of these various particles will vary in size, shape, homogeneity, texture, and adhesion properties.

As shown in FIG. 1, the sheath fluid (8) is forced into the nozzle chamber (11) surrounding the sample tube or sample introduction element (9) at the same time that the sample is injected through the sample tube into the nozzle chamber. Both fluids travel down the chamber with the sample remaining in the center of the chamber. In an ideal sorting-type of setup the sample particles travel in line to the orifice where they exit a microscopic nozzle orifice or nozzle aperture (13) (typically 50–250 microns) into the free fall area within which droplets form and fall. Generally, at this point, the characteristics of the sample are determined at high speeds, sometimes as rapidly as 40,000 drops per second. In the typical application, the samples are then sorted at high speeds into containers based upon the detected characteristics. Thus, predictability and consistency are crucial to accurate detection and to accurate sorting of the samples. Unwelcome variations in the stream emanating from the nozzle, either in volume or in direction or both, may have significant effects on the ability of the user to provide accurate results.

In practice, particles and gas in the sheath fluid or nozzle aperture adherents or the sample particles injected into the nozzle chamber accumulate faster that they can exit the nozzle and can begin filling the nozzle chamber or occluding the nozzle aperture with sample particles or gas bubbles. This accumulation of particles or gas can cause partial or total clogs in the nozzle or nozzle aperture. FIGS. 1, 2 and 3 show a typical cytometer nozzle or exterior surface of a flow cytometer nozzle and area in which such clogging may occur. The problem of clogged nozzles also causes problems relating to the limited shelf life of samples which may be biological in nature and any delays relating to equipment malfunction may require completely starting an experiment from scratch.

Another source of nozzle clogs is related to homogeneity of the sample. The sample preparer, for some reason, may be unable to filter the sample prior to sorting it on the cytometer or the filtered samples may agglutinate. In this case, some of the particles may be larger than the nozzle orifice which will immediately cause clogs.

More specifically, significant advances on sorting sperm for a variety of purposes have been made in recent years. Yet, this type of sample is especially prone to clogging. At present, the only quantitative technique used to achieve the separation of X- and Y-chromosome bearing sperm has been that involving individual discrimination and separation of the sperm through the techniques of flow cytometry. This technique appeared possible as a result of advances and discoveries involving the quantitative dye absorption of X-and Y-chromosome bearing sperm. This was discussed early in U.S. Pat. No. 4,362,246 and significantly expanded upon through the techniques disclosed by Lawrence Johnson in U.S. Pat. No. 5,135,759. The Johnson technique of utilizing flow cytometry to separate X- and Y-chromosome bearing sperm has been so significant an advancement that it has for the first time made the commercial separation of such sperm feasible. While still experimental, separation has been significantly enhanced through the utilization of high speed flow cytometers such as the MoFlo® flow cytometer produced by Cytomation, Inc. and discussed in a variety of other patents including U.S. Pat. Nos. 5,150,313, 5,602,039, 5,602,349, and 5,643,796 as well as international PCT patent publication WO 96/12171. While the utilization of Cytomation's MoFlo® cytometers has permitted great increases in speed, and while these speed increases are particularly relevant given the high number of sperm often used, certain problems have still remained. In spite of the almost ten-fold advances in speed possible by the MoFlo® flow cytometer, shorter and shorter sorting times have been desired for several reasons. First, it has been discovered that as a practical matter, the sperm are time-critical cells. Their fertility decreases with increased delay time. Second, the collection, sorting, and insemination timings has made speed an item of high commercial importance. Thus, the time critical nature of the sperm cells and the process has made speed an essential element in achieving high efficacy and success rates. Naturally, clogging which greatly increases the time required for sorting of the sperm, can be debilitating to the entire success of the process.

Clogging can also occur from the particular sheath fluid used in cytometry operations. The sheath fluid typically used on a cytometer is that of a saline solution including other additives as needed. This saline may form salt crystals on the outside on the nozzle orifice and slowly restrict the exit orifice of the nozzle or otherwise disturb the natural spraying direction of the nozzle. This may result in a partial or complete clog of the nozzle, and can exacerbate problems caused by sample clumping.

Perhaps one of the most significant problems that those in some fields have faced is that of clearing the orifice of the nozzle without damaging it in some way. While this basic concept seems quite simple, implementation is not so straightforward. The operator or other user was faced with the decision to attempt unclogging in situ while it is attached to the cytometer and properly aligned or to remove the nozzle, clean it and then restart the very tedious and slow realignment steps which are necessary if the nozzle is removed before it can be used again for sorting.

One concept put forward for clearing a nozzle in situ involves inserting a thin wire or similar device into the orifice of the nozzle. While this may seem quite straightforward, the problem of finding the orifice of the nozzle which may be 50 to 250 microns in diameter is quite difficult. Further the small diameter of the wire would make it far too delicate to practically thread into the orifice. Another complication to this approach is the small and difficult-to-reach area where a cytometer nozzle is typically located on the instrument. Even if the aforementioned problems were overcome, the nozzle would likely become damaged as a result of the insertion.

Another concept which has been discussed involves the use of applying a vacuum from the outside of the nozzle orifice, which suffers from a clog or particle. This approach has practical limitations involving sealing around the exterior of the nozzle to allow a vacuum to develop. A vacuum source would need to be generated of sufficient magnitude to be of benefit to the nozzle. This approach is complicated by touching the nozzle in situ and thereby disturbing its sensitive alignment and flow path. Potentially, the vacuum source could make a nozzle clog worse by pulling the particulates inside the nozzle closer and packing them harder into the orifice. Even if a nozzle is unclogged by this method, the operator might be forced to realign the cytometer before using the cytometer.

Another concept used solely in the context of analytical cytometers which do not form droplets is the use of a piezoelectric crystal to set up localized vibrations around the sample injector or sensing aperture for declogging. This concept, shown in U.S. Pat. No. 4,673,288 however, has never been developed or applied for a system compatible with the unique requirements of drop flow cytometry for dislocation of particles. Moreover, the disclosure of using oscillations with respect to analytical flow cytometry teaches the use of pressure change to dislocate gas which teaches away from the disclosed invention.

Another problem particular to cytometry and addressed by this invention is that of trapped air bubbles or gas in the fluidic components of a cytometer. The bubbles can form a compressible medium in the nozzle chamber that affects the precision alignment of the flow stream. In practice,the bubbles are sometimes difficult to remove from the chamber or de-bubble the chamber due, perhaps, to surface tension of the bubble to the walls of the chamber and within the sheath fluid itself. An operator generally is delayed in processing the sample through the cytometer when bubbles are present in the nozzle chamber, thus reducing the efficiency of the process. The cytometer operator previously had no tool to address the problem of trapped gases and had no choice but to wait some amount of time, which would vary greatly, and allow the bubbles to naturally migrate to areas of lesser concern.

Another concern particular to drop flow cytometry systems is in situ cleaning of either the exterior or the interior of the drop flow cytometer nozzle. Adherents which collect on the nozzle disturb the flow path and alignment with the flow path sensing system. Routine cleaning of the nozzle surfaces can maintain the flow path and alignment parameters without having to disassemble the nozzle and clean the parts separate from the drop flow cytometer. Previously, no tool existed to address the problem of cleaning such surfaces of the drop flow cytometer nozzle.

As to both the cytometry industry and the overall desire to unclog nozzles in situ in any industry, the present invention discloses techniques which overcome virtually every one of the previous problems in a practical fashion. Perhaps surprisingly, it satisfies a long-felt need to achieve unclogging, de-bubbling and cleaning of a nozzle in situ with little or no damage to the nozzle and without significantly disturbing it in any way. It is perhaps surprising to those involved in the use of cytometers to see how the problem could be solved in a safe, economical manner without requiring the removal of nozzles.

III. DISCLOSURE OF INVENTION

The present invention includes a variety of aspects which may be selected in different combinations to suit the needs of the user. First, it can function as a nozzle unclogging tool or cleaning tool for a cytometer nozzle or any nozzle which has been partially clogged. Second, it can be used as an unclogging tool for a cytometer nozzle or any nozzle which has become fully clogged or has a particle entrapped. In a basic form, the concept involves taking a source of vibratory energy or using an energy converter which creates mechanical oscillations (as selected with a oscillation selection element or by sweeping a range of oscillations), and with a media or oscillation coupling element present (such as a fluid, gel or other appropriate media) or through a mechanical couple, and transferring the energy from the source and presenting (coupling) it to the problem area or to allow the media in cooperation with the vibration (either ultrasonic or subsonic) to dislodge any matter in the nozzle which may be causing the clog. Such a technique offers advantages to the operator of the cytometer in allowing machine downtime and any resulting realignment to be greatly reduced, thereby making the operation of a cytometer to be more predictable and increasing the likelihood of successfully sorting a particular sample. Third, it can function as a de-bubbling tool to aid the cytometer operator in removing bubbles from a cytometer. This device excites the nozzle and surrounding fluid in such a way that the air quickly migrates to areas where it can be removed. The invention does this by providing a means for a vibratory chamber of media in which to immerse the nozzle, especially the orifice of the nozzle, into the vibrating media in the chamber while the nozzle is still mounted and fluidically attached or by means of mechanical coupling to the exterior surfaceof the nozzle.

Based upon testing which has occurred to date, it functions particularly well on partially clogged nozzles. It appears to typically unclog these nozzles and allow the cytometer stream to return to its original position, thereby eliminating the need for adjustment, so typical prior to the present invention.

One of the broad objects of the invention is to allow for an unclogging tool or portable member configured so as to mechanically couple mechanical oscillations to the exterior of the nozzle to be used while the nozzle is present on the cytometer, in situ. Thus, one goal includes making the device small enough to fit within the existing spaces surrounding the nozzle on cytometers. Another goal would be to allow a means for the device to be moved into position or have a portable member such that the chamber or portable surface configured so as to mechanically couple mechanical oscillations to the exterior of the nozzle is presenting the vibratory media to the nozzle orifice or nozzle exterior and then easily removed from this area such that normal cytometer functions can take place. This goal may be accomplished manually (hand held) such as with a portable device or may be automated with a more permanently mounted unit or automated movement that retracts and engages the nozzle. Likewise, it may be manually activated independent of flow cytometer operation conditions when the operator notices a variation in the processing or it may be automated by sensors detecting a clogging or in response to flow cytometer conditions.

Another goal would be to allow the use of such a device that will not harm the nozzle. A goal for this invention is to unclog the nozzle while preventing any aspects to the procedure which could effect the positioning of the nozzle or the original condition of the nozzle orifice.

Another broad object of the invention is to provide a means of removing air bubbles from the nozzle or debubbling. Some of the goals for this object remain the same as for unclogging in that the device is generally small enough to fit in the space allowed and may be easily moved out of the way after use. A further goal would be to allow the cytometer operator to pull a vacuum on the inside of the nozzle chamber while presenting a surface configured so as to mechanically couple mechanical oscillations to the exterior of the nozzle or a chamber of media to the nozzle and vibrating the media and therefore the nozzle with sufficient energy that any air bubbles in the nozzle will no longer cling to the sides of the nozzle, but will rise to areas where they may removed through fluidic hoses and tubes.

Yet another goal would be to allow for different cytometer nozzles on different cytometer machines to be unclogged and debubbled with this invention. Further, it is a goal to provide this in an economical manner such that it is affordable to the cytometry user.

IV. BRIEF DESCRIPTION OF THE DRAWINGS

V. BEST MODE FOR CARRYING OUT THE INVENTION

The preferred embodiment is that of a probe or portable member which includes a surface configured to mechanically couple oscillation to the exterior of the flow cytometer nozzle or a cavity which holds a media (such as a fluid, gel, or other appropriate energy transferring media) which creates a bath or oscillations coupling element which may be vibrating. This cavity is presented to the nozzle, especially the orifice area, and allows the nozzle orifice to be at least partially immersed into the bath where any undesirable material may be removed or cleaned or the energy may be used for other purposes such as removing air bubbles from the nozzle.

Figure 1:
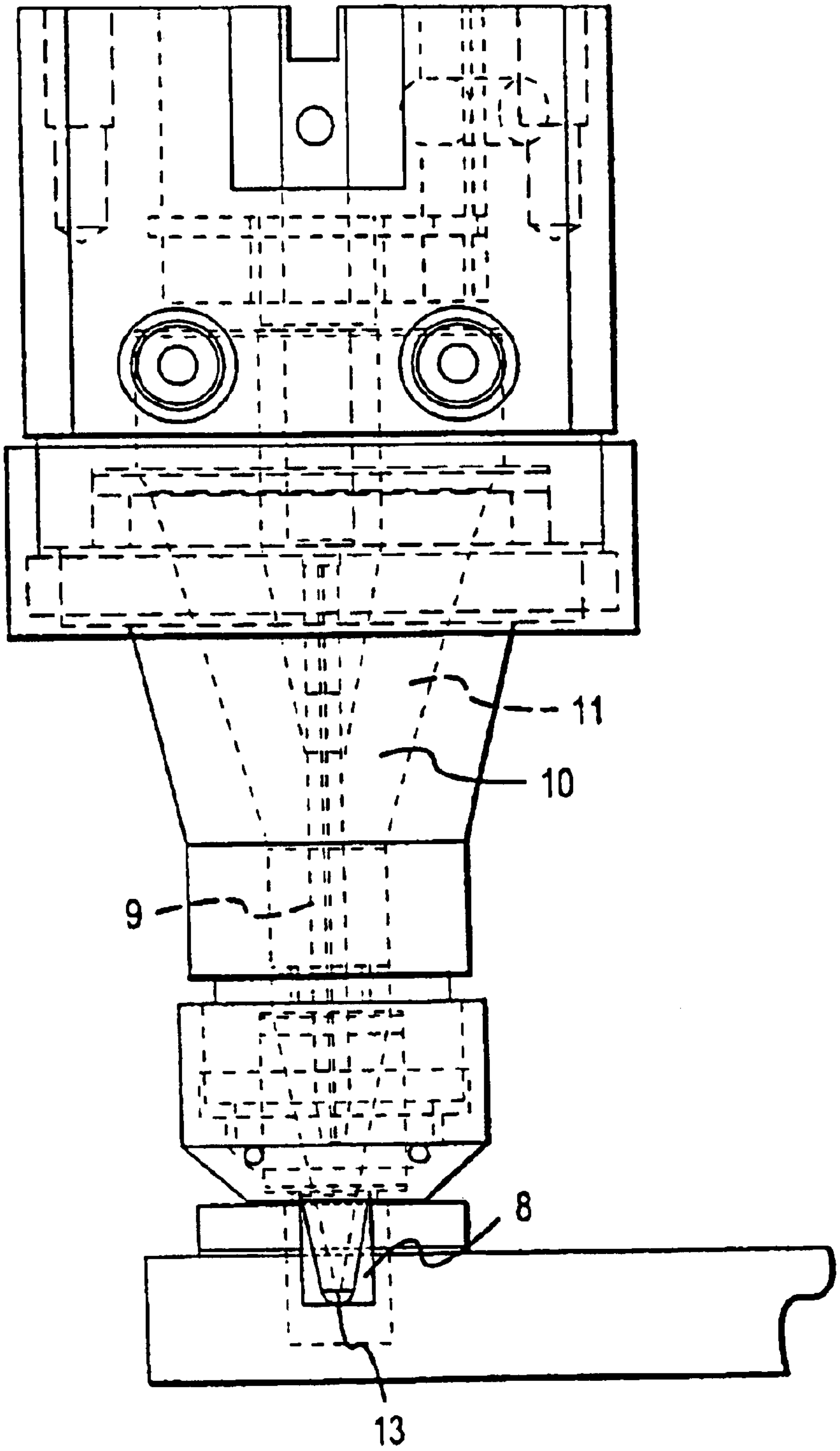
FIG. 1 is a side view of a nozzle assembly showing the sample tube, inner cavity, sheath fluid, orifice and the positioning of a oscillating portable member, oscillation coupling element, and fluid retaining element.
Figure 2:
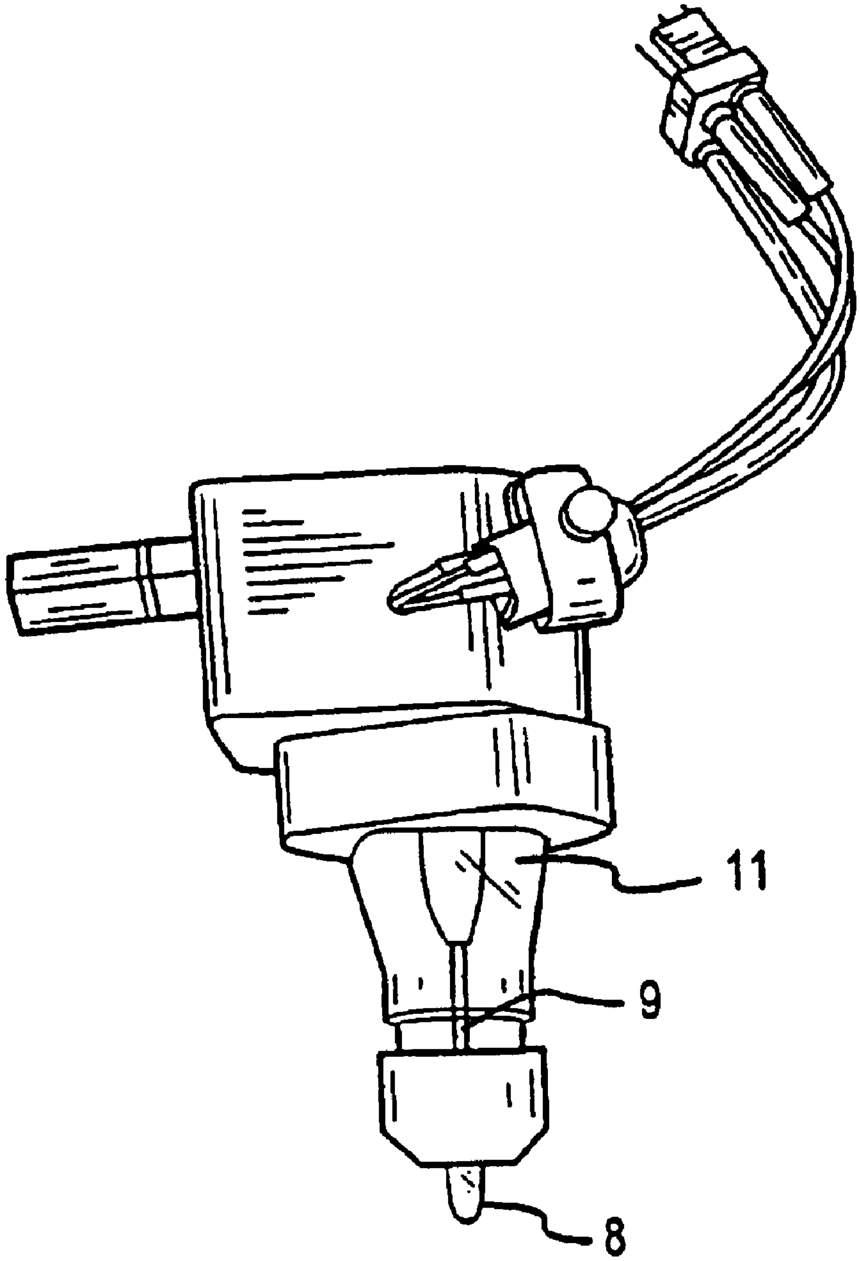
FIG. 2 is a photo of a typical drop flow cytometer nozzle assembly, showing on one end the nozzle through which is an orifice which may become clogged.
Figure 3:
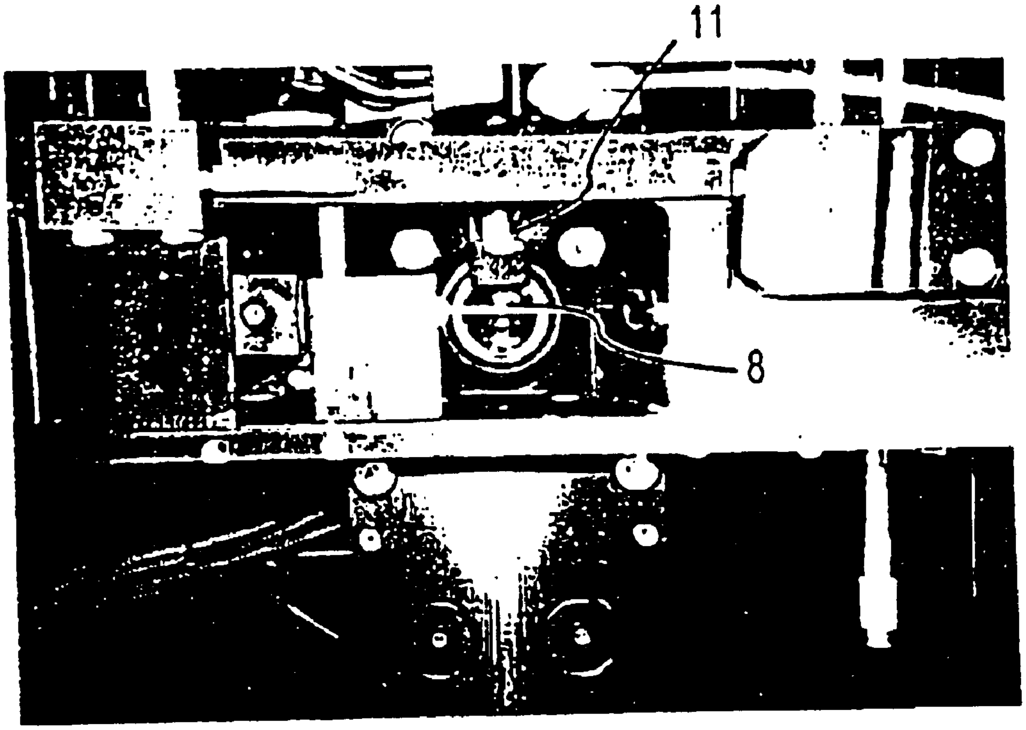
FIG. 3 is a photo of a typical cytometer and a nozzle in situ where it would become clogged.
Figure 4:
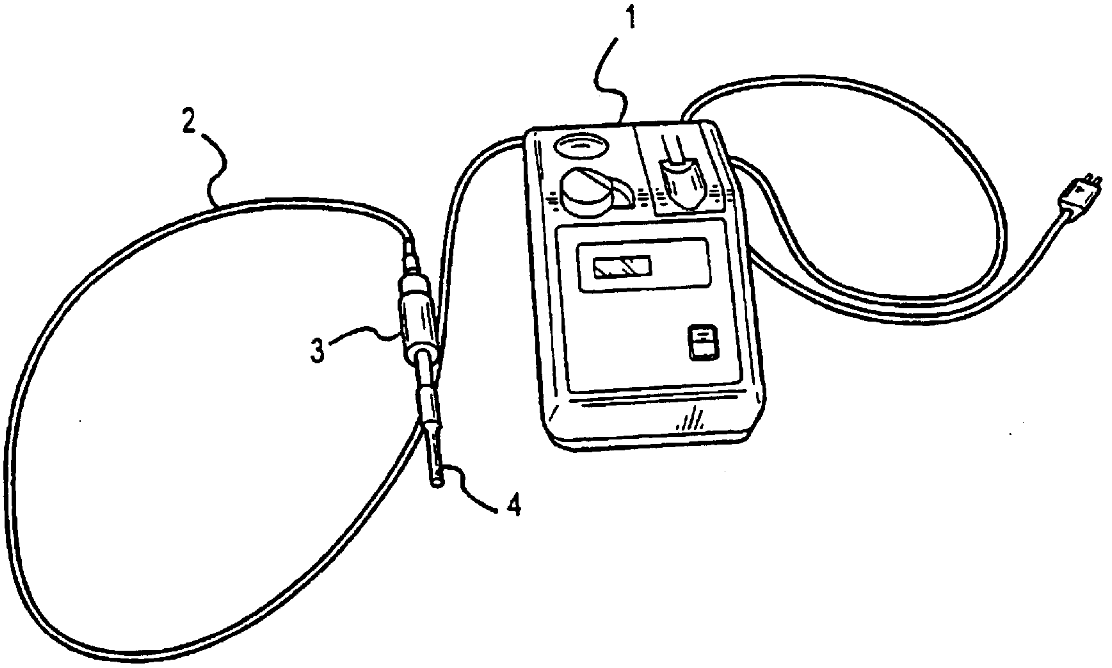
FIG. 4 is a photo of the preferred embodiment being portable and having a vibration generator or energy source (1), flexible cable transfer element (2), and energy converter (3) which may be used to provide energy to the probe or portable member (4).
Figure 5:
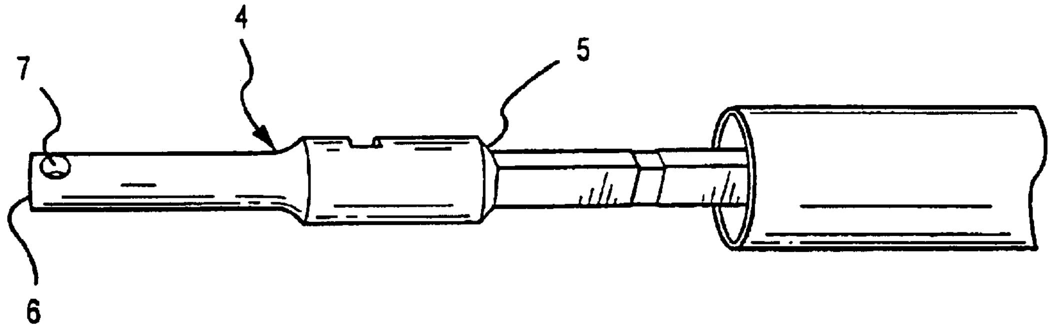
FIG. 5 is a photo of a probe or portable member (4) which is one embodiment of the invention which has a cavity or cup surface (7), an attachment end or joining element (5), and activating end (6).
Figure 6:
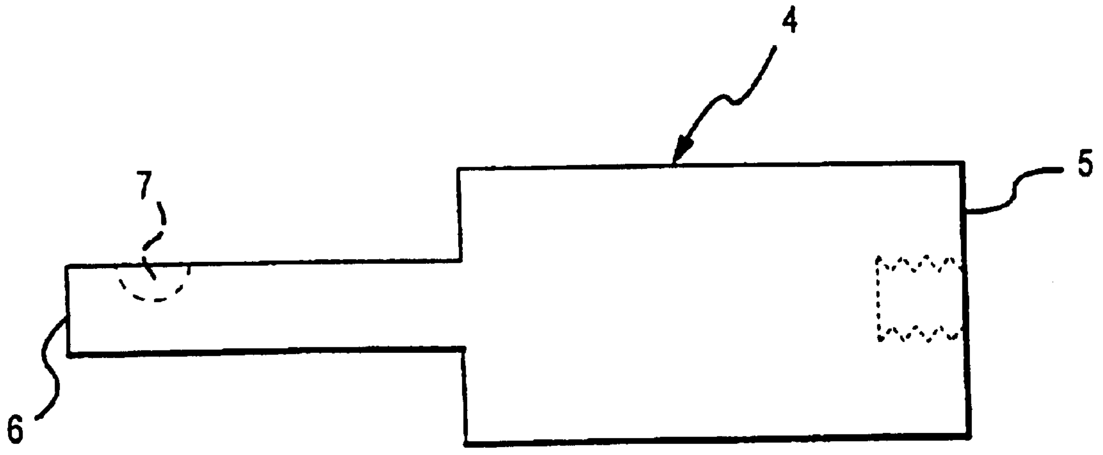
FIG. 6 is a sketch of a side view of a probe (4) showing the cavity cup surface (7), an attachment end (5), and activating end (6).

As shown in FIG. 4, part of the unit involves a source of vibrating energy, or vibration generator or energy converter (1), available from a variety of suppliers as would be known to those of ordinary skill in the art. This generator may develop a variety of frequencies of selected or varying amplitudes designed to optimally excite the probe (that is for coupling oscillations to the exterior of the nozzle body that has specific selectable parameters such as a cleaning parameter, a gas dislocations parameter, or particle disintegration parameter, or sperm cell sorting, or alternately are chosen by sweeping a range of oscillations). In the preferred embodiment, the vibration generator will have a amplitude and/or frequency adjustment or oscillation variation element or oscillation selector element which allows the operator to set or select the desired power level or sweep a range of oscillations prior to or during use (this can be critical as at least some particles and gas will have oscillation parameters that are highly dependant on flow cytometer operating conditions). The vibration generator or energy source or driver system (1) may be connected to a flexible cable or transfer element (2), as shown in FIG. 4, which conducts the electrical signals to an energy converter or oscillation system (3). The cable or transfer element may be flexible to allow the user to move the energy converter to the using area and of sufficient length to not require moving the vibration generator. The energy converter (3) turns the electrical energy from the vibration generator or drive system or energy source into mechanical energy of vibration or mechanical oscillations and can be connected to the attachment end (5) of the probe or portable device (4). The energy converter may in turn be connected to a mechanically isolated receptacle so that the energy converter may be hand held. In the preferred embodiment, the attachment end of the probe may be circular in cross section and has a female thread or joining element in it which allows the probe to be attached to the energy converter. The attachment end (5) of the probe may be circular to eliminate any thin walled sections of the probe which might be susceptible to cracking from stresses caused by the axial vibration of the probe. As would be known to those with skill in the art, the probe (4) is tuned by varying the dimensions of or selecting or sweeping the frequency of the vibration generator (1). In one embodiment for a cytometer nozzle, the probe may have an overall length of approximately 4–5 inches. The activating end (6) of the probe having the cavity or surface configured to the exterior surface of the flow cytometer nozzle or surface configured to cup a nozzle tip (7) may be approximately 0.5 inches high and approximately 0.3 inches wide. The cavity itself can be adjusted for a variety of nozzles and could be a hole approximately 0.25 inches in diameter and slightly less than the 0.5 inches height of the probe and can have or be a self alignment element for self alignment with the nozzle surface or a plurality interchange portable members with surfaces configured to approximately match portions of the exterior of the nozzle surface which may be attached and detached with a joining element.

Probe Material

In the preferred embodiment, the probe (4) may be constructed of titanium. This material transmits the energy developed by the energy converter (3) efficiently. Further, it has sufficient stiffness to allow the probe to reflect the vibration energy back to the converter and develop various modes of vibration along the axis of the probe. This attribute allows the probe to be optimized such that sufficient energy is developed in the cavity (7), allowing the media in the cavity to be vibrationally excited to an optimum amount which effectively cleans the nozzle orifice while substantially maintaining the media in the cavity or in conjuction with a fluid retaining element. This material further has the advantage of not easily oxidizing or corroding when presented to saline and other fluids commonly used in conjunction with cytometers. This material is commonly used to make ultrasonic vibration probes by the manufacturers of such devices which are employed to do functions such as ultrasonic welding and forming of material.

In the preferred embodiment, the user would determine that the device is needed for a debubbling or unclogging operation and would fill the probe cavity with a cleaning media. This media may be water, saline, or other fluid, compatible with cytometers. It may also be a gel or solid which might remain in the cavity with some stability. Naturally, it could be a variety of other media, including a granular or even a solid media in appropriate instances. After filling the cavity (7) in the probe (4) while holding the energy converter (3) horizontally with the cavity facing upward, the operator could switch on the vibration generator and set or select or variably sweep the power level to the desired setting. The operator could then hold or hand hold the converter such that the nozzle orifice or nozzle exterior is at least partially immersed by the media or oscillation coupling element in the cavity and also adjoins at least part of the interior surface of the nozzle. The operator could hold the energy converter in this position for a time period such as a few seconds. While doing this operation the fluid lines going into the nozzle could remain pressurized. A liquid evacuation element could remove liquid from the cup so that the flow cytometer could be operated while coupled to the portable member. The operator could then move the converter such that the probe is not obstructing the normal spray path of the nozzle. The operator could then ascertain whether the nozzle was spraying normally or whether all air bubbles had been removed, and if not, repeat the operation.

In the preferred embodiment, the source of vibratory energy, the vibration generator (1), flexible cable (2), and energy converter (3) together may be provided as a readily available, off the shelf component to reduce costs.

Figure 7:
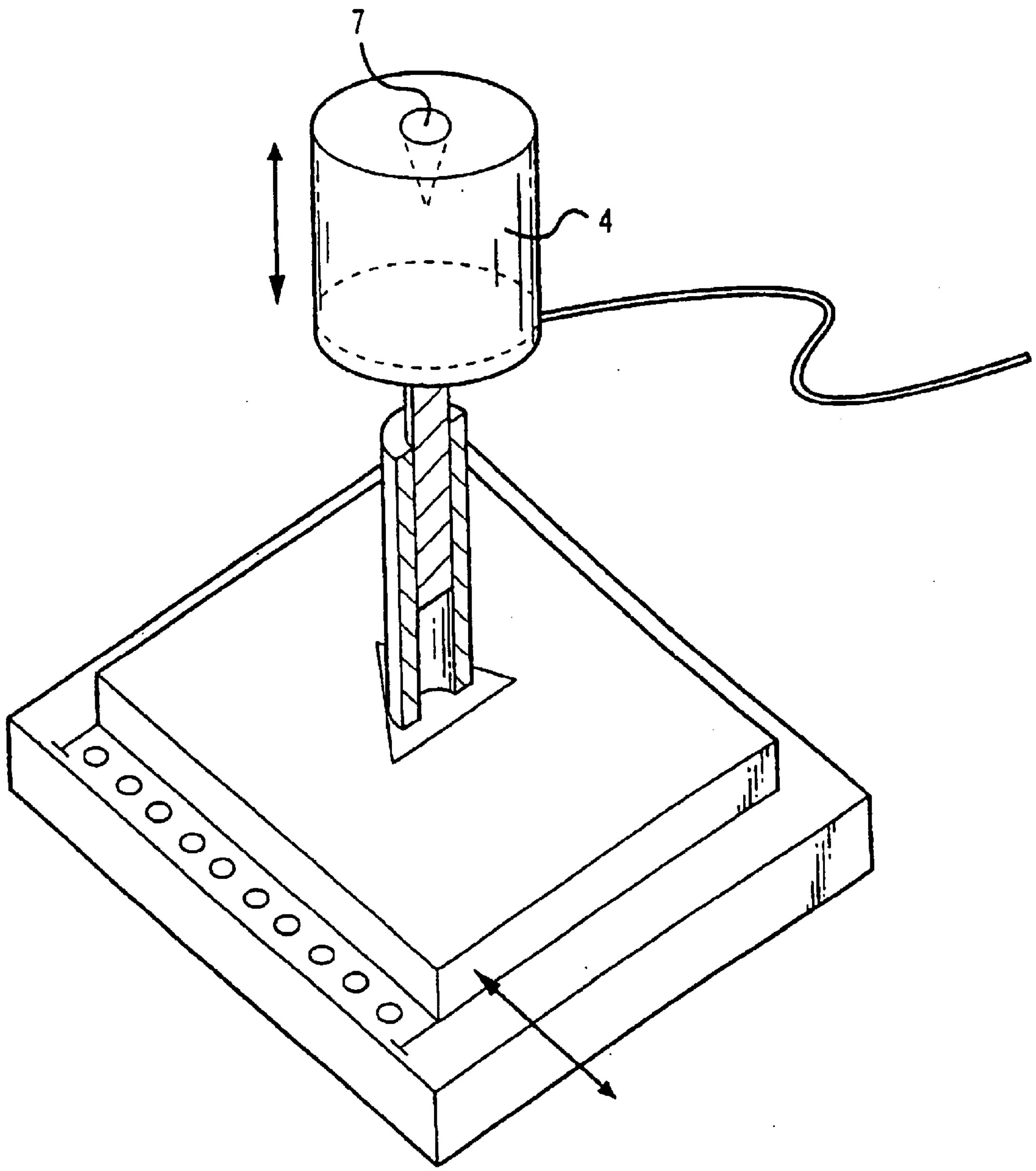
FIG. 7 is a sketch of a probe (4) and cavity or cup surface (7) as part of an alternative embodiment being more of a permanent installation which may be mounted to a cytometer and which allows these components to move to the nozzle area and then be moved aside.

Another embodiment is that of a cavity or cup or energy converter which is designed to be part of an instrument or product. This may be accomplished by using a first driver system for drop formation operation and a second driver circuit to drive the same drop formation oscillation system at different selected oscillation parameters or sweep a range of oscillations parameters so as to provide gas dislocation, particle disintegration, and cleaning parameters. Alternately, a second oscillation system driven by the second driver system could be employed. As shown in FIG. 7, the cavity (7) and probe or portable member (4) may be attached to a moving member or automated movement which could be moved to an area near the nozzle for any unclogging or debubbling operations and then moved out of the way. As would be known to those with skill in the art, such an arrangement could be mounted to the cytometer or some adjacent surface. It could be retractably placed at an indexed position to engage the cavity with the nozzle and then removed after attempting the declogging or debubbling. Such an arrangement could include hydraulic positioning, electromechanical positioning (such as by sensors, slides, limit switches and so forth). The embodiment could be actuated or triggered by an activation element manually or independant of flow cytometer operation conditions by an operator or when a declogging situation is noticed. Alternatively, it could be actuated automatically or in response to flow cytometer conditions when a sensor senses a declogging situation, such as by a reduced flow, an aberration in the flow direction, and so forth. Also as shown in FIG. 7, the probe (4) can be of a variety of shapes or a plurality of interchangeable tools as might be appropriate to the particular configuration and purposes.

Another embodiment involves the use of a more solid transfer of the vibration energy to the nozzle such as through the probe or energy converter itself or through a solid media or compressible element with a three-dimension surface in or on the probe or energy converter. The vibrating object may be placed against the nozzle which may transfer vibratory energy to the nozzle which may be used for air bubble removal or excitation of the fluid inside the nozzle in such a way as to unclog, or to clean the nozzle.

Figure 8:
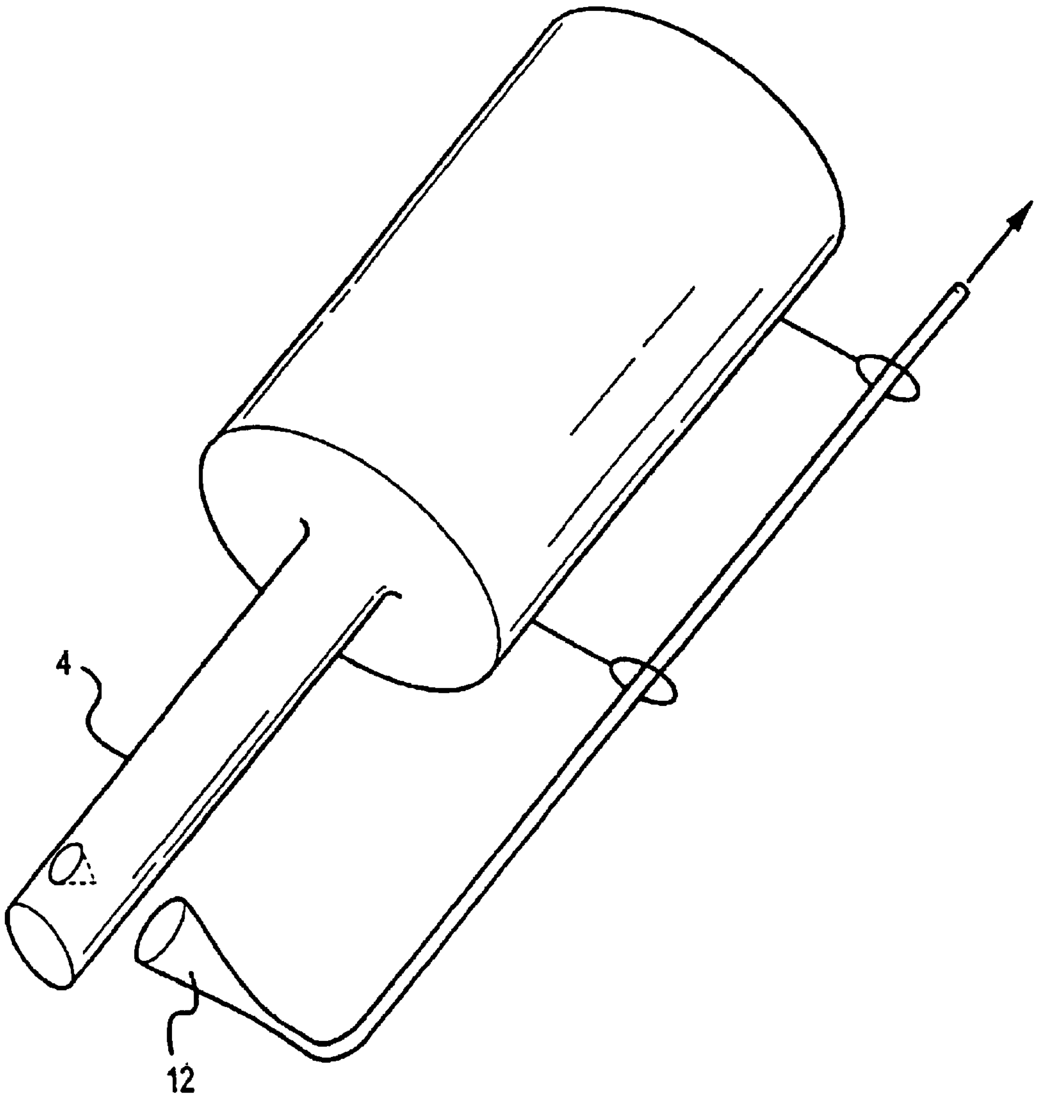
FIG. 8 is a sketch of a probe (4) with a media trap or instrument shield (12) and a liquid evacuation element ( ) which could be employed in an alternative embodiment to collect any liquids or media before they could collect in an unwanted area.

An alternative embodiment, shown in FIG. 8, includes a trap or droplet shield (12) for media which may be displaced from the cavity when the nozzle is placed into the cavity. These materials, if not trapped, could land on high voltage components below the nozzle or on optical components or analysis system which acts at least in part as a result of events within the free fall area near the nozzle. The embodiment shown in FIG. 8 allows for a system and method of trapping these media before they become a problem. Of course, other embodiments could be employed to accomplish the same function.

In addition, it should be understood that, in the claims and in the application, the term "comprising" is meant to have an inclusive meaning rather than an exclusive one. It should be interpreted in its most expansive form so as to afford the applicant the broadest coverage legally permissible. Therefore, in countries, such as Australia, this term is not intended to have an exclusive, or more limited, meaning.

The discussion included in this application is intended to serve as a basic description. The reader should be aware that the specific discussion may not explicitly describe all embodiments possible; many alternatives are implicit. The marketplace and manufacturing concerns may dictate the appropriate embodiments for the present invention. Particularly with respect to the discussion, it should be understood that a number of changes may be made without departing from the essence of the present invention. In this regard, it is intended that such changes—to the extent that they substantially achieve the same results in substantially the same way—will still fall within the scope of the present invention. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus discussions or claims may not only be included for the device described, but also method or process claims may be included to address the functions the invention and each element performs. Although the methods related to the system are being included in various detail, only an initial discussion directed toward the declogging/debubbling device have been included. Naturally, that discussion could have some application to the various other methods and apparatus discussed throughout the disclosure.

This is particularly true for the present invention since its basic concepts and understandings may be broadly applied. Neither the description nor the terminology is intended to limit the scope of the claims. invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure.

It should be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure.

In addition, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all action may be expressed as a means for taking that action or as an element which causes that action. Similarly, each physical element disclosed should be understood to encompass a disclosure of the action which that physical element facilitates. Regarding this last aspect, the disclosure of a "vibration generator" should be understood to encompass disclosure of the act of "vibrating" whether explicitly discussed or not—and, conversely, were there only disclosure of the act of "vibrating" such a disclosure should be understood to encompass disclosure of a "vibration generator" or a "vibrator." Such changes and alternative terms are to be understood to be explicitly included in the description.

Any references such as patents mentioned in the application for this patent as well as any references listed in any information disclosure filed with the application are hereby incorporated by reference; however, to the extent statements might be considered inconsistent with the patenting of this/these invention(s) such statements are expressly not to be considered as made by the applicant(s). Finally, it should also be understood that as to the claims the various combinations and permutations of each of the claims are possible.

What is claimed is:

1. A portable oscillating device for a flow cytometer which oscillates an exterior surface of a flow cytometer nozzle, comprising:

a. a source of energy;

b. a transfer element coupled to said source of energy;

c. an energy converter coupled to said transfer element which creates mechanical oscillations; and d. a portable member configured so as to mechanically couple said mechanical oscillations to said exterior surface of said flow cytometer nozzle.

2. A portable oscillating device for a flow cytometer which oscillates an exterior surface of a flow cytometer nozzle as described in claim 1 and further comprising a mechanically isolated receptacle connected to said portable member.

3. A portable oscillating device for a flow cytometer which oscillates an exterior surface of a flow cytometer nozzle as described in claim 2 wherein said mechanically isolated receptacle connected to said portable member is hand held.

4. A portable oscillating device for a flow cytometer which oscillates an exterior surface of a flow cytometer nozzle as described in claim 3 and further comprising a compressible coupling element affixed to said portable member which has at least one three dimensional surface.

5. A portable oscillating device for a flow cytometer which oscillates an exterior surface of a flow cytometer nozzle as described in claim 3 and further comprising a cup surface of said portable member configured to cup an exterior surface of a nozzle tip of said flow cytometer nozzle.

6. A portable oscillating device for a flow cytometer which oscillates an exterior surface of a flow cytometer nozzle as described in claim 5 and further comprising an oscillation coupling element held within said cup surface of said portable member configured to cup said exterior surface of said nozzle tip of said flow cytometer nozzle.

7. A portable oscillating device for a flow cytometer which oscillates an exterior surface of a flow cytometer nozzle as described in claim 6 wherein said oscillation coupling element held within said cup surface of said portable member configured to cup said exterior surface of said nozzle tip of said flow cytometer nozzle comprises a solid material.

8. A portable oscillating device for a flow cytometer which oscillates an exterior surface of a flow cytometer nozzle as described in claim 6 wherein said oscillation coupling element held within said cup surface of said portable member configured to cup said exterior surface of said nozzle tip of said flow cytometer nozzle comprises a liquid material.

9. A portable oscillating device for a flow cytometer which oscillates an exterior surface of a flow cytometer nozzle as described in claim 8 and further comprising a fluid retaining element with a first side affixed to said portable member and a second side which conforms to said exterior of said flow cytometer nozzle with said first side and said second side and said cup surface of said portable member configured to cup said exterior surface of said flow cytometer nozzle.

10. A portable oscillating device for a flow cytometer which oscillates an exterior surface of a flow cytometer nozzle as described in claim 9 and further comprising a liquid evacuation element connected to said cup surface of said portable member configured to cup said exterior surface of said nozzle tip of said flow cytometer to remove liquid from said cup surface of said portable member configured to cup said exterior surface of said nozzle tip of said flow cytometer nozzle.

11. A portable oscillating device for a flow cytometer which oscillates an exterior surface of a flow cytometer nozzle as described in claim 3 and further comprising a joining element of said portable member wherein said joining element removably joins said portable member and said energy converter.

12. A portable oscillating device for a flow cytometer which oscillates an exterior surface of a flow cytometer nozzle as described in claim 11 and further comprising a plurality of interchangeable portable members wherein each said interchangeable portable member has a nozzle exterior matching surface which mechanically couples with a corresponding matching surface of said exterior surface of said flow cytometer nozzle.

13. A portable oscillating device for a flow cytometer which oscillates an exterior surface of a flow cytometer nozzle as described in claim 3, 5, 8, 9 or 10 and further comprising an automated movement to which said mechanically isolated receptacle is responsive which couples said portable member configured so as to mechanically couple said mechanical oscillations to said exterior surface of said flow cytometer nozzle with said exterior surface of said flow cytometer nozzle.

14. A portable oscillating device for a flow cytometer which oscillates an exterior surface of a flow cytometer nozzle as described in claim 13 and further comprises an activation circuit connected to said automated movement which activates said automated movement independent of flow cytometry operation conditions.

15. A portable oscillating device for a flow cytometer which oscillates an exterior surface of a flow cytometer nozzle as described in claim 13 and further comprising an activation circuit connected to said automated movement which activates said automated movement in response to flow cytometer operation conditions.

16. A drop flow cytometer system, comprising:

a. a portable oscillating device as described in claim 15;

b. a sheath fluid;

c. a nozzle body within which at least a portion of said sheath fluid is contained;

d. a sample introduction element contained within said nozzle body;

e. an oscillation system to which said sheath fluid is responsive and which acts to create droplets;

f. a first driver system to which said oscillation system is responsive;

g. a second driver system to which said oscillation system is responsive;

h. a free fall area within which said droplets form and fall;

i. an analysis system acting at least in part as a result of events within said free fall area; and j. a sort system responsive to said analysis system which acts upon said droplets in said free fall area.

17. The drop flow cytometer system of claim 16 and further comprising a second energy converter which creates mechanical oscillations coupled to said exterior surface of said flow cytometer nozzle.

18. The drop flow cytometer system of claim 16 and further comprising a droplet shield coupled to said drop flow cytometer system between said exterior surface of said flow cytometer nozzle that forms droplets and an instrument surface of said flow cytometer system.

19. A portable oscillating device for a flow cytometer which oscillates an exterior surface of a flow cytometer nozzle as described in claim 2 or 3 and further comprising a self alignment guide integral to said portable member which allows said portable member to self align with said exterior surface of said flow cytometer nozzle.

20. A portable oscillating device for a flow cytometer which oscillates an exterior surface of a flow cytometer nozzle as described in claims 1, 3, 5, 8, 9, or 10 and further comprising an oscillation selection element which drives said energy converter at one of multiple selectable oscillation parameter.

21. A portable oscillating device for a flow cytometer which oscillates an exterior surface of a flow cytometer nozzle as described in claim 20 wherein said oscillation selection element drives said energy converter at a selectable oscillation parameter which corresponds to a nozzle aperture cleaning parameter.

22. A portable oscillating device for a flow cytometer which oscillates an exterior surface of a flow cytometer nozzle as described in claim 20 wherein said oscillation selection element drives said energy converter at a selectable oscillation parameter which corresponds to a particle disintegration parameter.

23. A portable oscillating device for a flow cytometer which oscillates an exterior surface of a flow cytometer nozzle as described in claim 20 wherein said oscillation selection element drives said energy converter at a selectable oscillation parameter which corresponds to a gas dislocation parameter.

24. A drop flow cytometer system, comprising:

a. a portable oscillating device as described in claim 20;

b. a sheath fluid;

c. a nozzle body within which at least a portion of said sheath fluid is contained;

d. a sample introduction element contained within said nozzle body;

e. an oscillation system to which said sheath fluid is responsive and which acts to create droplets;

f. a first driver system to which said oscillation system is responsive;

g. a second driver system to which said oscillation system is responsive;

h. a free fall area within which said droplets form and fall;

i. an analysis system acting at least in part as a result of events within said free fall area; and j. a sort system responsive to said analysis system which acts upon said droplets in said free fall area.

25. The drop flow cytometer system of claim 24 and further comprising a second energy converter which creates mechanical oscillations coupled to said exterior surface of said flow cytometer nozzle.

26. The drop flow cytometer system of claim 24 and further comprising a droplet shield coupled to said drop cytometer system between said exterior surface of said flow cytometer nozzle that forms droplets and an instrument surface of said flow cytometer system.

27. A portable oscillating device for a flow cytometer which oscillates an exterior surface of a flow cytometer nozzle as described in claims 1, 3, 5, 8, 9, or 10 and further comprising an oscillation variation element which drives said energy converter over a range of oscillations.

28. A drop flow cytometer system, comprising:

a. a portable oscillating device as described in claim 27;

b. a sheath fluid;

c. a nozzle body within which at least a portion of said sheath fluid is contained;

d. a sample introduction element contained within said nozzle body;

e. an oscillation system to which said sheath fluid is responsive and which acts to create droplets;

f. a first driver system to which said oscillation system is responsive;

g. a second drive system to which said oscillation system is responsive;

h. a free fall area within which said droplets form and fall;

i. an analysis system acting at least in part as a result of events within said free fall area; and j. a sort system responsive to said analysis system which acts upon said droplets in said free fall area.

29. The drop flow cytometer system of claim 28 and further comprising a second energy converter which creates mechanical oscillations coupled to said exterior surface of said flow cytometer nozzle.

30. The drop flow cytometer system of claim 29 and further comprising a droplet shield coupled to said drop flow cytometer system between said exterior surface of said flow cytometer nozzle that forms droplets and an instrument surface of said flow cytometer system.

31. A drop flow cytometer system, comprising:

a. a portable oscillating device as described in claims 1, 3, 5, 8, 9, or 10;

b. a sheath fluid;

c. a nozzle body within which at least a portion of said sheath fluid is contained;

d. a sample introduction element contained within said nozzle body;

e. an oscillation system to which said sheath fluid is responsive and which acts to create droplets;

f. a first driver system to which said oscillation system is responsive;

g. a second driver system to which said oscillation system is responsive;

h. a free fall area within which said droplets form and fall;

i. an analysis system acting at least in part as a result of events within said free fall area; and j. a sort system responsive to said analysis system which acts upon said droplets in said free fall area.

32. The drop flow cytometer system of claim 31 and further comprising a second energy converter which creates mechanical oscillation coupled to said exterior surface of said flow cytometer nozzle.

33. The drop flow cytometer system of claim 31 and further comprising a droplet shield coupled to said drop flow cytometer system between said exterior surface of said flow cytometer nozzle that forms droplets and an instrument surface of said flow cytometer system.

34. A drop flow cytometer system, comprising:

a. a sheath fluid;

b. a nozzle body within which at least a portion of said sheath fluid is contained;

c. a sample introduction element contained within said nozzle body;

d. an oscillation system to which said sheath fluid is responsive and which acts to create droplets;

e. a first driver system to which said oscillation system is responsive;

f. a second driver system to which said oscillation system is responsive;

g. a free fall area within which said droplets form and fall;

h. an analysis system acting at least in part as a result of events within said free fall area; and i. a sort system responsive to said analysis system which acts upon said droplets in said free fall area.

35. A drop flow cytometer system as described in claim 34 wherein said first driver system and said second driver system have different oscillation parameters.

36. A drop flow cytometer system as described in claim 35 wherein said sheath fluid is responsive to said second driver system.

37. A drop flow cytometer system as described in claim 35 and further comprising an oscillation parameter selector which establishes said oscillation parameters.

38. A drop flow cytometer system as described in claim 37 wherein said oscillation parameter selector establishes said second driver system parameter at a nozzle cleaning parameter.

39. A drop flow cytometer system as described in claim 37 wherein said oscillation parameter selector establishes said second driver system parameter at a gas dislocation parameter.

40. A drop flow cytometer system as described in claim 37 wherein said oscillation parameter selector establishes said second driver system parameter at a particle disintegration parameter.

41. A drop flow cytometer system as described in claim 34 wherein said nozzle body has an exterior surface and wherein said oscillation system comprises:

a. a first oscillation system driven by said first driver system;

b. a second oscillation system driven by said second driver system;

c. a second oscillation system coupling element having an exterior oscillation surface coupled to said exterior surface of said nozzle body.

42. A drop flow cytometer system as described in claim 41 wherein said exterior surface of said second oscillation system coupling element is configured to complement said exterior surface of said nozzle body.

43. A drop flow cytometer system as described in claim 42 wherein said second oscillation system coupling element comprises a fluidic oscillation coupling element.

44. A drop flow cytometer system as described in claim 43 wherein said nozzle body has a nozzle aperture and wherein said fluidic oscillation coupling element couples said second oscillation system to said nozzle aperture of said nozzle body.

45. A drop flow cytometer system as described in claim 44 wherein said fluidic oscillation coupling element adjoins at least part of an internal surface of said nozzle aperture.

46. A drop flow cytometer system as described in claim 41 and further comprising an oscillation parameter selector which establishes oscillation parameters.

47. A drop flow cytometer system as described in claim 46 wherein said oscillation parameter selector establishes said second driver system at a nozzle cleaning parameter.

48. A drop flow cytometer system as described in claim 46 wherein said oscillation parameter selector establishes said second driver system at a gas dislocation parameter.

49. A drop flow cytometer system as described in claim 46 wherein said oscillation parameter selector establishes said second driver system at a particle disintegration parameter.

50. A drop flow cytometer system as described in claim 41 and further comprising an oscillation variation element to which said oscillation system is responsive.

51. A drop flow cytometer system as described in claim 37 or 50 wherein said oscillation system changes independent of drop flow cytometer operating conditions.

52. A drop flow cytometer system as described in claim 37 or 50 wherein said oscillation system automatically changes in response to drop flow cytometer operating conditions.

53. A drop flow cytometer system as described in claim 34 or 43 and further comprising an instrument protection shield which surrounds said nozzle body when said second driver system is activated.

54. A fluidic oscillation system for a flow cytometer which oscillates a flow cytometer nozzle exterior surface, comprising:

a. an energy source;

b. a energy transfer element coupled to said source of energy;

c. a energy converter connected to said energy transfer element and which creates mechanical oscillations; and d. a fluidic oscillation coupling element which is responsive to said energy converter and which fluidicly couples said mechanical oscillations to said flow cytometer nozzle exterior surface.

55. A fluidic oscillation system as described claim 54 and further comprising:

a. a sheath fluid;

b. a nozzle body within which at least a portion of said sheath fluid is contained;

c. a sample introduction element contained within said nozzle body;

d. an oscillation system to which said fluidic oscillation coupling element is responsive;

e. a free fall area below said flow cytometer nozzle exterior surface;

f. an analysis system acting at least in part as a result of events within said free fall area; and g. a sort system responsive to said analysis system.

56. A fluidic oscillation system as described in claim 55 and further comprising a flow cytometer nozzle interior surface and wherein said fluidic oscillation coupling element adjoins at least part of said flow cytometer interior surface.

57. A fluidic oscillation system as described in claim 56 and further comprising an oscillation parameter selection element which operates said energy converter at selectable oscillation parameters.

58. A fluidic oscillation system as described in claim 57 wherein said oscillation parameter selection element operates said energy converter at said selectable oscillation parameters corresponding to a nozzle aperture cleaning parameter.

59. A fluidic oscillation system as described in claim 57 wherein said oscillation parameter selection element operates said energy converter at said selectable oscillation parameters corresponding to a gas dislocation parameter.

60. A fluidic oscillation system as described in claim 57 wherein said oscillation parameter selection element operates said energy converter at said selectable oscillation parameters corresponding to a particle disintegration parameter.

61. A fluidic oscillation system as described in claim 57 wherein said oscillation parameter selection element operates said energy converter at said selectable oscillation parameters corresponding to a sperm break-up parameter.

62. A fluidic oscillation system as described in claim 54 and further comprising an oscillation variation element which operates said energy converter throughout a range of at least one oscillation parameter useful to the operation of said flow cytometer.

63. A oscillation system for a flow cytometer, comprising:

a. an energy source;

b. a energy transfer element coupled to said energy source;

c. A energy converter connected to said energy transfer element which outputs mechanical oscillations;

d. an oscillation variation system which operates said energy converter throughout a range of at least one oscillation parameter;

e. a sheath fluid;

f. a nozzle body within which at least a portion of said sheath fluid is contained;

g. a sample introduction element contained within said nozzle body;

h. an oscillation system which is responsive to said oscillation variation system;

i. a free fall area below an exterior surface of said nozzle body;

j. an analysis system acting at least in part as a result of events within said free fall area; and k. a sort system responsive to said analysis system.

64. A flow cytometer system as described in claim 63 wherein said nozzle body has an interior surface and wherein said oscillation variation system selects a cleaning oscillation to remove adherents from said interior surface of said nozzle body.

65. A flow cytometer system as described in claim 64 wherein said oscillation variation system selects a gas dislocation oscillations to dislocate gas entrapped within said nozzle body.

66. A flow cytometer system as described in claim 64 wherein said oscillation variation system selects a particle disintegration oscillation to disintegrate particles entrapped within said nozzle body.

67. A method of flow cytometry, comprising the steps of:

a. providing a flow cytometry apparatus having an exterior surface;

b. introducing a sample within said flow cytometry apparatus;

c. conducting flow cytometry through action of said flow cytometry apparatus;

d. engaging said exterior surface of said flow cytometry apparatus by a portable member;

e. creating oscillations within said flow cytometry apparatus through action of said portable member;

f. disengaging said portable member from said exterior surface of said flow cytometry apparatus; and g. continuing to conduct flow cytometry through action of said flow cytometry apparatus.

68. A method of flow cytometry as described in claim 67 and further comprising mechanically isolating said portable member.

69. A method of flow cytometry as described in claim 68 and further comprising the step of holding a mechanically isolated receptacle connected to said portable member in a hand to removably couple said oscillations to said exterior surface of said flow cytometer apparatus.

70. A method of flow cytometry as described in claim 69 and further comprising the step of compressing a coupling element to a portable surface of said portable member.

71. A method of flow cytometry as described in claim 70 and further comprising the step of cupping a cup surface of said portable member configured to approximate, the exterior dimensions of said exterior surface of said flow cytometer apparatus near said exterior surface of said flow cytometer apparatus.

72. A method of flow cytometry as described in claim 71 and further comprising the step of oscillating said exterior surface of said flow cytometer apparatus with an oscillation coupling element held within said cup surface.

73. A method of flow cytometry as described in claim 72 wherein said step of oscillating said exterior surface of said flow cytometer apparatus with an oscillation coupling element held within said cup surface comprises using a solid oscillation coupling element.

74. A method of flow cytometry as described in claim 72 wherein said step of oscillating said exterior surface of said flow cytometer apparatus with an oscillation coupling element held within said cup surface comprises the use of a liquid oscillation coupling element.

75. A method of flow cytometry as described in claim 74 wherein said flow cytometry apparatus has an interior surface and further comprising the step of fluidicly coupling said oscillations to said interior surface of said flow cytometry apparatus.

76. A method of flow cytometry as described in claim 74 and further comprising the step of draining fluid from said cup surface configured to approximate said exterior dimensions of said exterior surface of said flow cytometer.

77. A method of flow cytometry as described in claim 72 and further comprising the step of retaining said oscillation coupling element with a fluid retaining element having a first side affixed to said portable member and a second side which conforms to said exterior of said flow cytometer apparatus with said first side and said second side and said cup surface configured to cup said exterior surface of said flow cytometer apparatus.

78. A method of flow cytometry as described in claim 67, 68, 69, 71, 72 or 73 and further comprising the step of selecting said oscillations by selecting a parameter from an oscillation selection element.

79. A method of flow cytometry as described in claim 78 and further comprising the step of disintegrating a particle within said flow cytometer apparatus when said portable member is cupping said exterior surface.

80. A method of flow cytometry as described in claim 78 and further comprising the step of dislocating a gas within said flow cytometer apparatus when said portable member is cupping said exterior surface of said flow cytometer apparatus by selecting a gas dislocation oscillation from said oscillation selection element.

81. A method of flow cytometry as described in claims 78 and further comprising the step of moving said portable member with an automated moving system.

82. A method of flow cytometry as described in claims 67, 68, 69, 71, 72, or 75 and further comprising the step of sweeping a range of oscillations.

83. A method of flow cytometry as described in claims 82 and further comprising the step of moving said portable member with an automated moving system.

84. A method of flow cytometry as described in claims 67, 68, 69, 70, 71, 72, 75, or 77 and further comprising the step of moving said portable member with an automated moving system.

85. A method of flow cytometry as described in claim 84 and further comprising the step of manually activating said automated moving system.

86. A method of flow cytometry as described in claim 84 and further comprising the step of automatically activating said automated moving system in response to preselected flow cytometer operating parameters.

87. A flow cytometer system, comprising:

a. a flow cytometry apparatus;

b. an energy source;

c. a energy transfer element coupled to said energy source;

d. a de-bubbling energy converter connected to said energy transfer element which outputs mechanical oscillations selected to have a de-bubbling oscillation parameter corresponding to gas dislocation which dislocates gas bubbles with said de-bubbling oscillation parameter from within said flow cytometer apparatus; and e. a portable member configured so as to mechanically couple said mechanical oscillations to said flow cytometry apparatus.

88. A method of flow cytometry, comprising the steps of:

a. providing a flow cytometry apparatus having an exterior surface;

b. providing a source of energy;

c. transferring said energy through a transfer element;

d. converting said energy with an energy converter which outputs mechanical oscillations;

e. introducing a sample within said flow cytometry apparatus;

f. conducting flow cytometry through action of said flow cytometry apparatus; and g. fluidicly coupling said mechanical oscillations to said exterior surface of said flow cytometry apparatus.

89. A method of flow cytometry as described in claim 88 wherein said step of fluidicly coupling said mechanical oscillations to said exterior surface of said flow cytometry apparatus comprises the step of cupping a cup surface configured to approximate the exterior dimensions of said exterior surface of said flow cytometer apparatus near said exterior surface of said flow cytometer apparatus.

90. A method of flow cytometry as described in claim 89 and further comprising the step of fluid from draining said cup surface configured to approximate said exterior dimensions of said exterior surface of said flow cytometer.

91. A method of flow cytometry as described in claim 90 and further comprising the step of retaining an oscillation coupling element within a portable member cupping said exterior surface of said flow cytometer apparatus with a fluid retaining element having a first side affixed to said portable member and a second side which conforms to said exterior surface of said flow cytometer apparatus with said first side and said second side and said cup surface configured to cup said exterior surface of said flow cytometer apparatus.

92. A method of flow cytometry as described in claim 88 or 90 wherein said step of fluidicly coupling said mechanical oscillations to said exterior surface of said flow cytometry apparatus comprises using a solid.

93. A method of flow cytometry as described in claim 88 or 90 wherein said step of fluidicly coupling said mechanical oscillations to said exterior surface of said flow cytometry apparatus comprises using a liquid.

94. A method of flow cytometry as described in claim 93 wherein said step of fluidicly coupling said mechanical oscillations to said exterior surface of said flow cytometry apparatus comprises the step of fluidicly coupling said mechanical oscillations to an interior surface of said flow cytometer apparatus.

95. A method of flow cytometry as described in claim 88 and further comprising the step of selecting said mechanical oscillations created by said energy converter by selecting a parameter from an oscillation selection element.

96. A method of flow cytometry as described in claim 95 and further comprising the step of disintegrating a particle within said flow cytometer apparatus when a portable member is cupping said exterior surface.

97. A method of flow cytometry as described in claim 95 and further comprising the step of dislocating a gas within said flow cytometer apparatus when a portable member is cupping said exterior surface of said flow cytometer apparatus by selecting a gas dislocation oscillation from said oscillation selection element.

98. A method of flow cytometry as described in claim 95 and further comprising the step of sweeping a range of oscillations.

99. A method of flow cytometry as described in claim 95 and wherein said step of fluidicly coupling said mechanical oscillations to said exterior surface of said flow cytometry apparatus comprises the step of fluidicly coupling said mechanical oscillations to said exterior surface with an automated moving system.

100. A method of flow cytometry as described in claim 88 and wherein said step of fluidicly coupling said mechanical oscillations to said exterior surface of said flow cytometry apparatus comprises the step of fluidicly coupling said mechanical oscillation to said exterior surface with an automated moving system.

101. A method of flow cytometry as described in claim 100 and further comprising the step of manually activating said automated moving system.

102. A method of flow cytometry as described in claim 100 and further comprising the step of automatically activating said automated moving system in response to preselected flow cytometer operating parameters.

103. A method of flow cytometry, comprising the steps of:

a. providing a flow cytometry apparatus;

b. providing a source of energy;

c. transferring said energy through a transfer element;

d. converting said energy with an energy converter which creates mechanical oscillations;

e. selecting a de-bubbling oscillation parameter corresponding to gas dislocation which dislocates gas bubbles with said de-bubbling oscillation parameter from within said flow cytometer apparatus;

f. creating de-bubbling oscillations within said flow cytometry apparatus using said de-bubbling oscillation parameter;

g. introducing a sample within said flow cytometry apparatus; and h. conducting flow cytometry through action of said flow cytometry apparatus.

104. A method of flow cytometry as described in claim 103 wherein said step of creating de-bubbling oscillations comprises the step of sweeping a range of oscillations.

* * * * *

UNITED STATES PATENT AND TRADEMARK OFFICE

CERTIFICATE OF CORRECTION

PATENT NO. : 6,746,873 B1
APPLICATION NO. : 09/622621
DATED : June 8, 2004
INVENTOR(S) : Kristopher S. Buchanan et al.

It is certified that error appears in the above-identified patent and that said Letters Patent is hereby corrected as shown below:

In the Claims,

Claim 63, column 15, line 61, “a energy transfer” should read -- an energy transfer --

Claim 63, column 15, line 63, “A energy converter” should read -- an energy converter --

Signed and Sealed this
Twenty-third Day of December, 2014

Michelle K. Lee
*Deputy Director of the United States Patent and Trademark Office*